(12) United States Patent
Reznik

(10) Patent No.: US 8,075,520 B2
(45) Date of Patent: Dec. 13, 2011

(54) ARTHROSCOPIC FLUID CONTROL DEVICE AND METHOD FOR CONTROLLING FLUID FLOW IN ARTHROSCOPIC PROCEDURES

(76) Inventor: Alan M. Reznik, Woodbridge, CT (US)

( * ) Notice: Subject to any disclaimer, the term of this patent is extended or adjusted under 35 U.S.C. 154(b) by 0 days.

(21) Appl. No.: 12/805,684

(22) Filed: Aug. 13, 2010

(65) Prior Publication Data

US 2010/0324473 A1  Dec. 23, 2010

Related U.S. Application Data

(63) Continuation-in-part of application No. 11/730,944, filed on Apr. 5, 2007, now Pat. No. 7,785,287.

(60) Provisional application No. 60/789,598, filed on Apr. 6, 2006.

(51) Int. Cl.
*A61M 29/00* (2006.01)
*A61M 1/00* (2006.01)
*A01G 25/16* (2006.01)

(52) U.S. Cl. .......... 604/96.01; 604/31; 604/35; 137/625

(58) Field of Classification Search ................ 604/31, 604/35; 137/625
See application file for complete search history.

(56) References Cited

U.S. PATENT DOCUMENTS

| | | | |
|---|---|---|---|
| 2,764,181 A | 9/1956 | Richolt | |
| 4,461,052 A | 7/1984 | Mostul | |
| 4,535,821 A | 8/1985 | Anderson | |
| 4,935,005 A * | 6/1990 | Haines | 604/30 |
| 4,940,457 A | 7/1990 | Olson | |
| 5,322,506 A | 6/1994 | Kullas | |
| 5,328,456 A | 7/1994 | Horiguchi et al. | |
| 5,484,402 A * | 1/1996 | Saravia et al. | 604/35 |
| 5,643,302 A | 7/1997 | Beiser et al. | |
| 5,810,770 A * | 9/1998 | Chin et al. | 604/65 |
| 5,944,054 A | 8/1999 | Saieva | |
| 6,602,221 B1 * | 8/2003 | Saravia et al. | 604/31 |
| 7,033,334 B2 | 4/2006 | Samolyk | |
| 2005/0283150 A1 | 12/2005 | Moutafis et al. | |
| 2007/0068573 A1 | 3/2007 | Cox et al. | |
| 2007/0202608 A1 | 8/2007 | Uffenheimer et al. | |

* cited by examiner

*Primary Examiner* — Nicholas Lucchesi
*Assistant Examiner* — Ian Holloway
(74) *Attorney, Agent, or Firm* — Welsh Flaxman & Gitler LLC

(57) ABSTRACT

A fluid control device is attached to tubes carrying irrigation solution to form the system. The control device splits the flow through a fiber optic scope and a fluid control unit. The fluid control unit controls rate of flow and direction. The operator utilizing a fluid rate and flow direction control device easily controls the flow of fluid into the joint, out of the joint, or no flow. The increased flow prevents collapse of a joint space and maintains clear visualization. The fluid flow solely relies on a gravity feed by having a fluid reservoir positioned at a high point in the system. It contains no fluid pump, vacuum or electronic controller while safely and reliably performing the functions of more complex devices.

10 Claims, 27 Drawing Sheets

Fig. 19
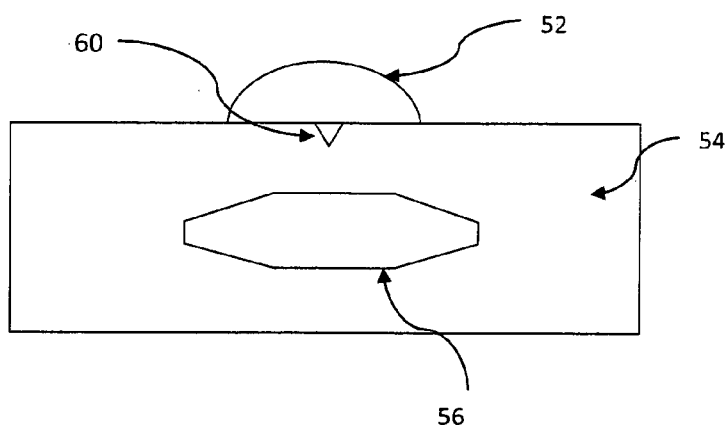
Fig. 19a
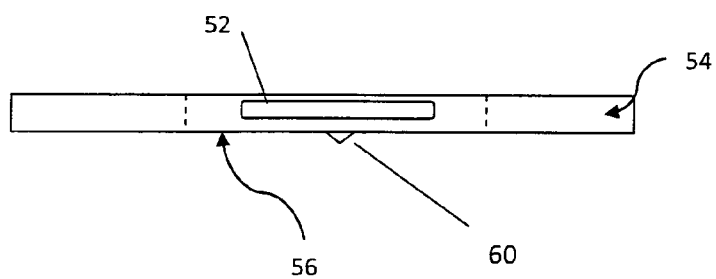
Fig. 19b

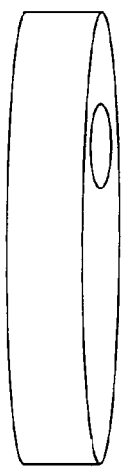
Fig. 23a
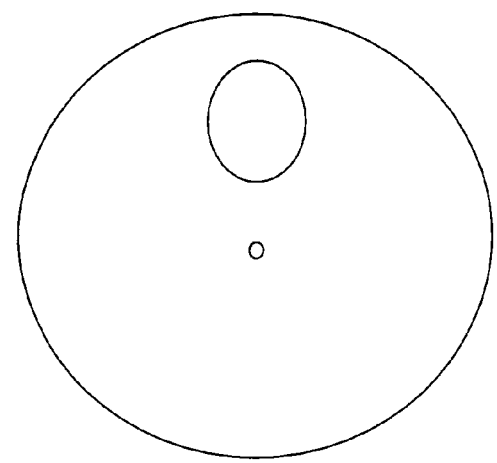
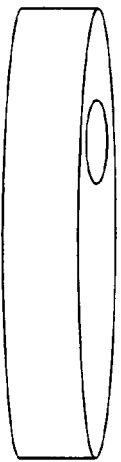
Fig. 23b
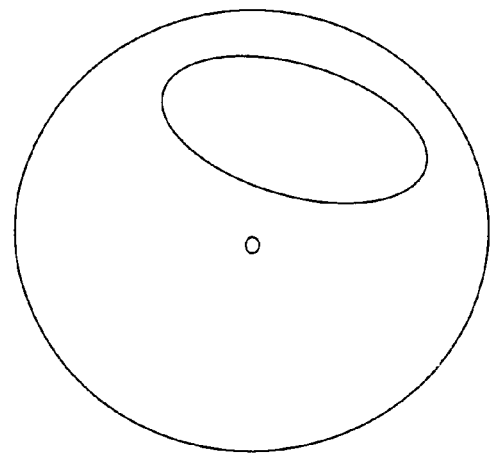
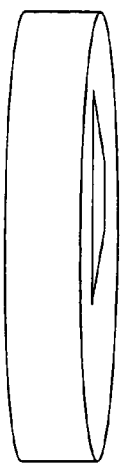
Fig. 23c
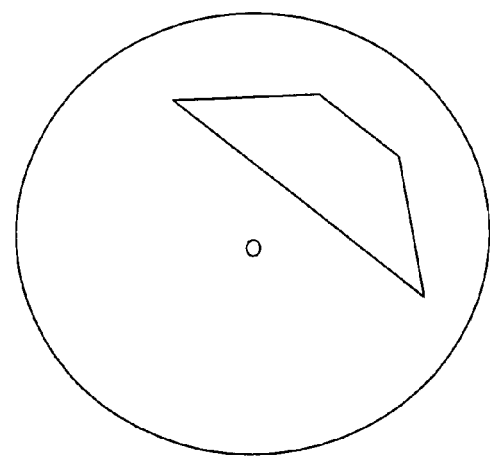

Fig. 23d
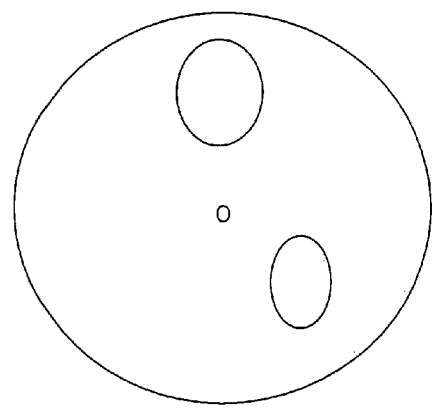
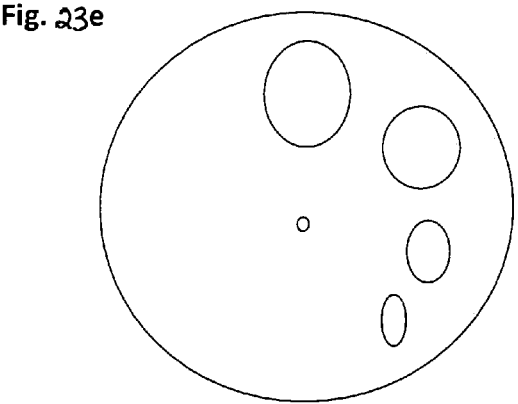
Fig. 23e
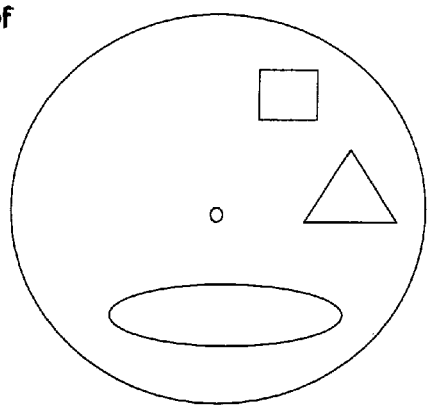
Fig. 23f

US 8,075,520 B2

ARTHROSCOPIC FLUID CONTROL DEVICE AND METHOD FOR CONTROLLING FLUID FLOW IN ARTHROSCOPIC PROCEDURES

This application is a continuation-in-part of U.S. patent application Ser. No. 11/730,944, filed Apr. 5, 2007, now U.S. Pat. No. 7,785,287 which claims the benefit of U.S. Provisional Application Ser. No. 60/789,598, filed Apr. 6, 2006.

BACKGROUND OF THE INVENTION

During arthroscopic surgery the flow of fluids and suction to the site must be controlled based on the surgeon's needs. Normally, fluid control is achieved with the use of a mechanical pump. Mechanical pumps have high initial costs plus maintenance costs and there is always the possibility that, during surgery, a pump will fail. There is always a risk of electric conduction injury and a risk of compartment syndrome where fluid pressure in a compartment exceeds venous pressure causing a loss of circulation to a limb or muscle group. This risk can be even greater with some of the current mechanical fluid systems when fluid leaks into spaces outside the joint as occurs in acute trauma when there is communication between the joint and local soft tissue. The invention gravity controlled positive pressure, in combination with the various modes of flow, reduces this risk and can eliminate the need for a tourniquet, thereby also reducing tourniquet related injuries due to vascular compromise and postoperative lactic acid accumulation in a limb. More recently electronic controls for fluid devices have been shown to have faulty electronics and/or problematic software leading to FDA recalls of these devices, mandatory service calls or upgrades to avoid patient injury. These concerns raise the inherent cost of these devices and add the requirement of significant post-market surveillance while in use.

There is a need in the art for a fluid control device not relying on a mechanical pump, vacuum, elaborate feedback loops, constant service, programming updates or elaborate electronic controls that provides adequate flow, control of direction of the flow and control of the flow rate.

Existing electromechanical system are based on constant pressure or constant flow. Some devices have extra feedback loops or pressure controls that must be properly maintained and serviced for reliable use and patient safety. The invention has distinct advantages over such a system because it only replenishes fluid that flows out of the joint, decreasing the amount of soft tissue swelling during the course of the procedure. Also, the gravity based system creates positive pressure environment in the joint to decrease intraarticular bleeding. Also, the system has multiple modes of flow allowing for more ways to clear intraarticular debris in the joint. By virtue of the simplistic design and control apparatus, this is all possible without the use of an electronic controller, pump, vacuum or elaborate mechanical or electronic feedback loop.

SUMMARY OF THE INVENTION

The fluid control device is attached to tubes carrying irrigation solution to form the system. The control device splits the flow through a fiber optic scope and a fluid control unit. The fluid control unit controls rate of flow and direction. The flow of fluid into the joint, out of the joint, or no flow is easily controlled by the operator. The device also allows for one or more inflows, and or more than one outflow. This is useful when using suction or suction shaving devices or when the joint space is small and fluid rate or direction control can aid in visualization. The increased flow prevents collapse of a joint space and maintains clear visualization. The fluid flow relies on gravity by having a fluid reservoir positioned at a high point in the system. The device can be configured in a number of novel ways to provide fluid control for rate and direction into and out of any number of cannulas, ports, or arthroscopic instruments. The fluid can be provided by a single or multiple fluid bags or reservoirs.

BRIEF DESCRIPTION OF THE DRAWINGS

FIGS. 19*a* and 19*b* show views of the slider device of the control device;

FIGS. 23*a*, 23*b*, 23*c*, 23*d*, 23*e* and 23*f* display a side view of variations of the slider device;

DETAILED DESCRIPTION OF THE INVENTION

Figure 1:
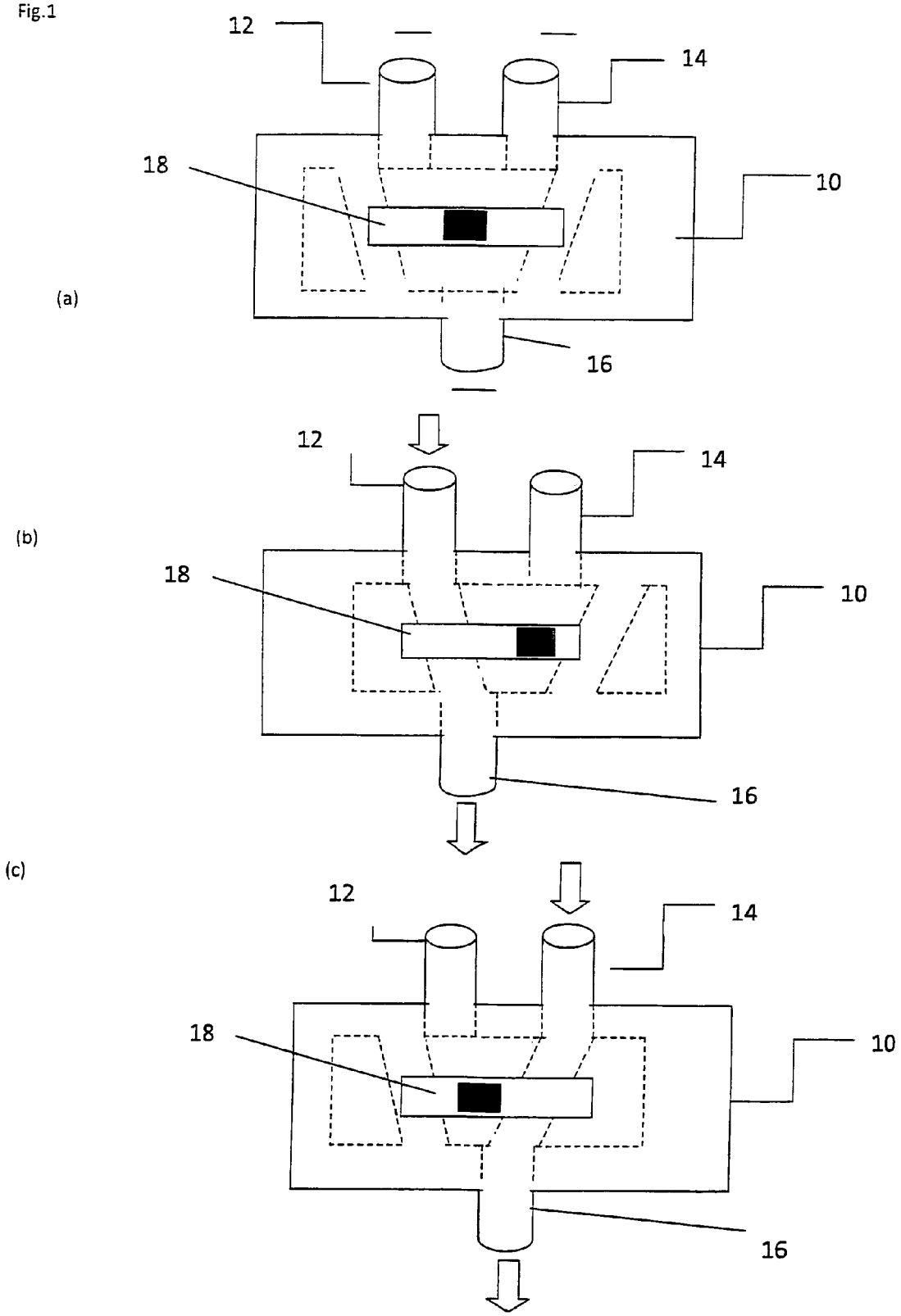
FIG. 1 shows the fluid control device in each of three positions.

FIG. 1 shows a fluid control device 10 having three ports 12, 14, 16. A slider is positioned between the two ports 12, 14. In FIG. 1A, the slider 18 is in the central position and there is no fluid communication between any ports. In FIG. 1B, the slider is moved to the right position and fluid flows between ports 12 through port 16. In FIG. 1C, a slider is moved to the left position and there is fluid communication between the port 16 and port 14.

Figure 2:
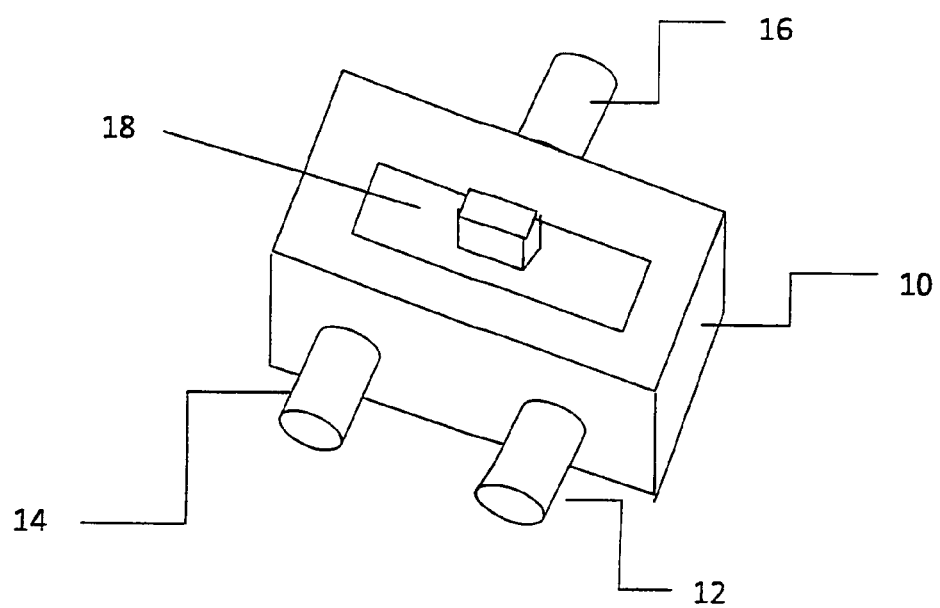
FIG. 2 shows views of the fluid control device.

FIG. 2 shows the front rear end perspective view of the fluid control device. In the front view, the slider and port 16 are seen. In the rear view, the ports 12 and 14 are seen, as well as the slider. This perspective view shows all three ports 12, 14, 16 and the slider 18.

Figure 3:
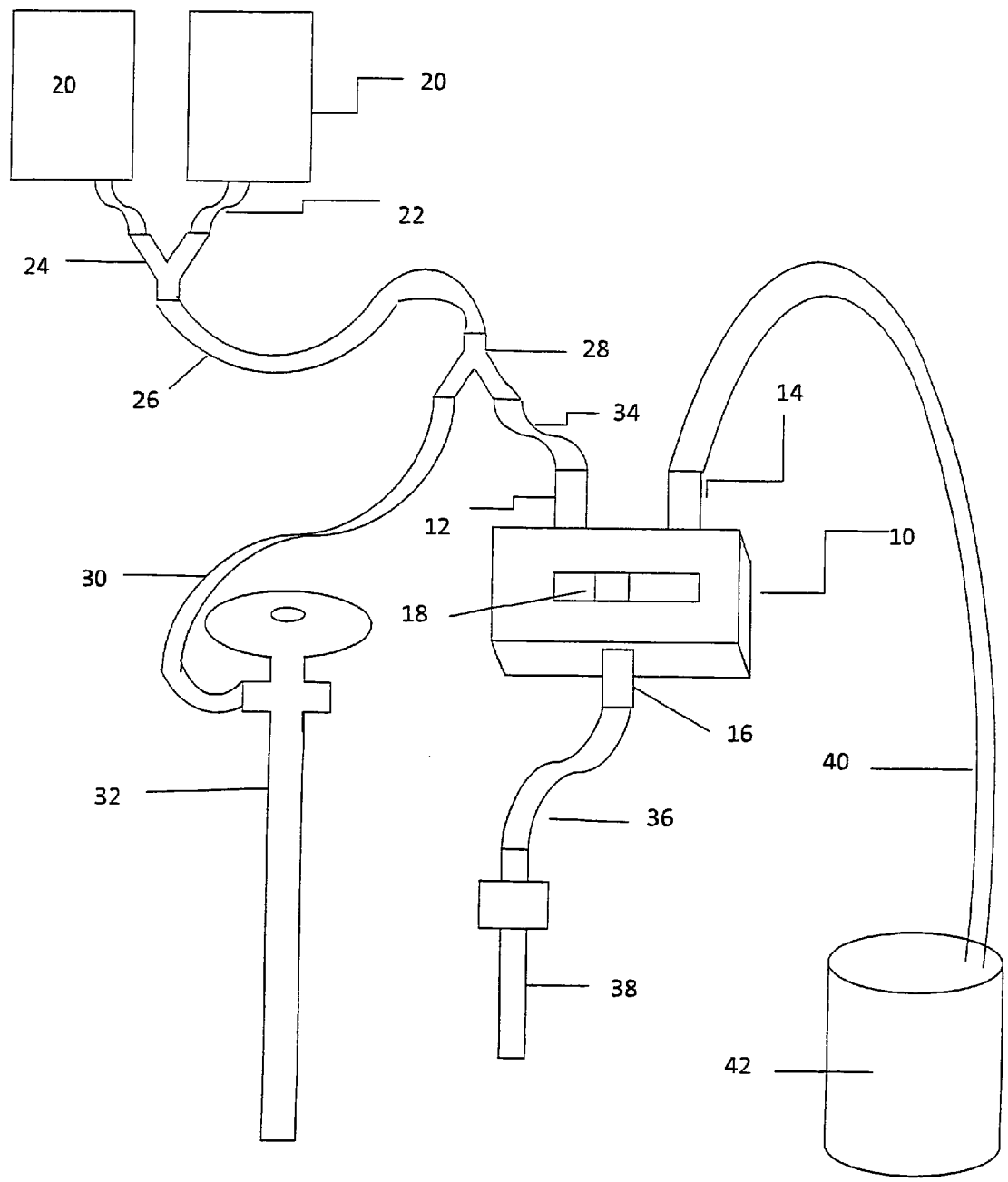
FIGS. 3-8 show the system in various modes used during surgery.

FIG. 3 shows the complete fluid control system, with fluid reservoirs 20 each having an outlet line 22 connected to a fluid divider, such as a Y junction 24, with line 26 leading from the Y junction 24 to a second Y junction 28. A single reservoir may be used which would be connected to the line 26. A first line 30 leads from the Y junction 28 to an arthroscope 32. A second line 34 extends from the Y junction 28 to the port 12 on the fluid control device 10. Leading from the port 16 is a line 36 terminating in a flow port cannula 38. A drain line 40 is connected to port 14 and leads to a gravity drainage 42.

Figure 4:
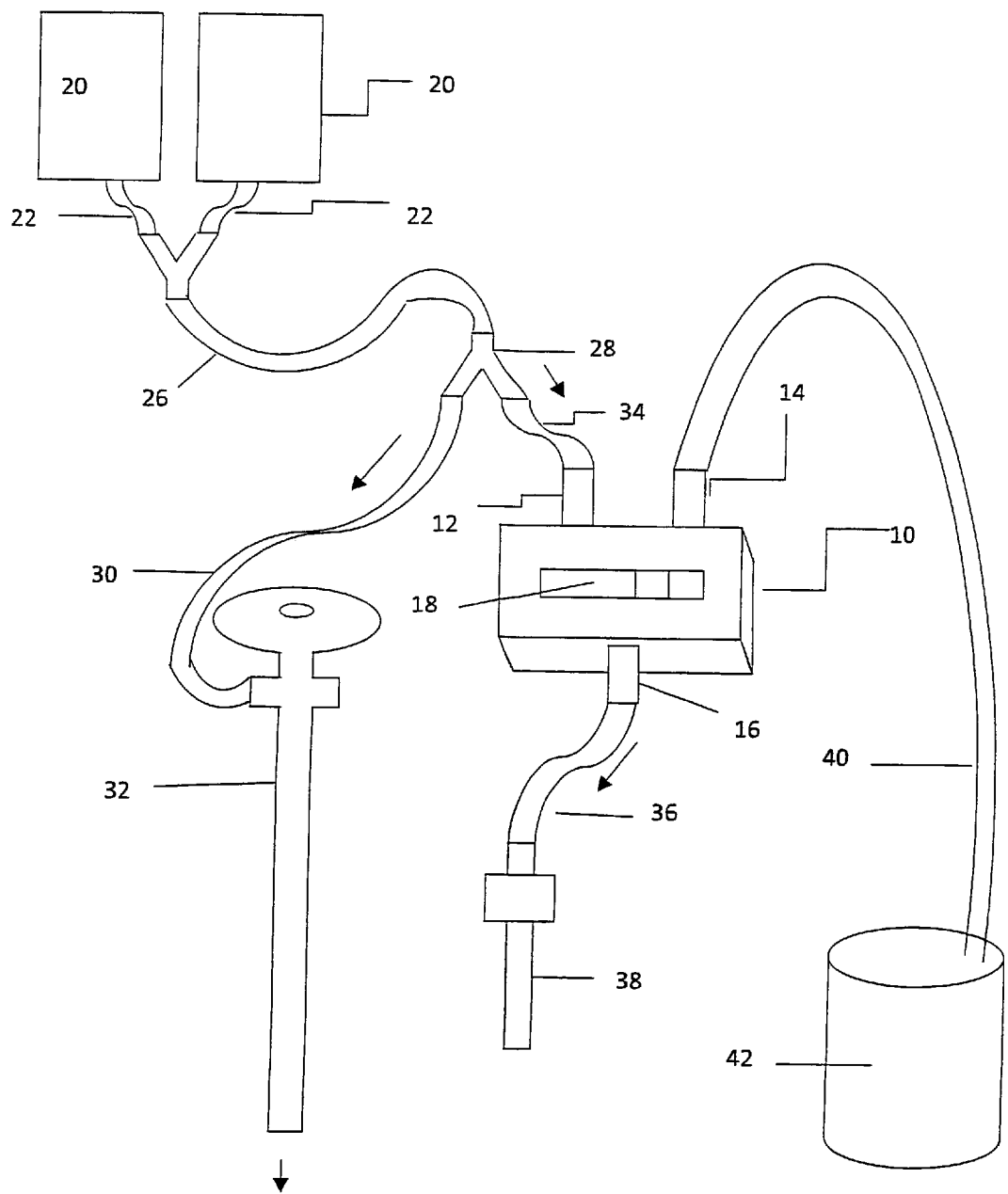
Figure 5:
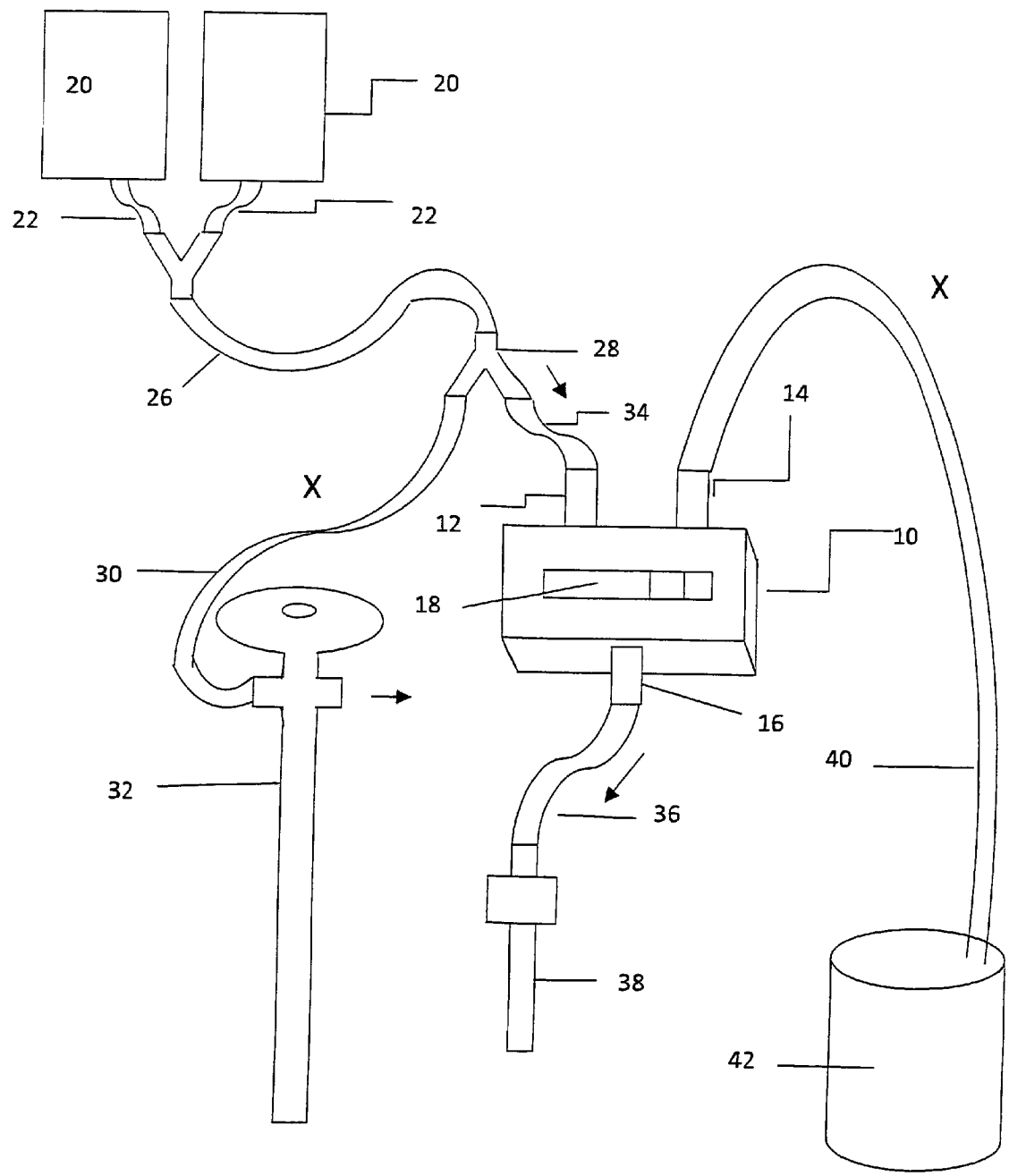
Figure 6:
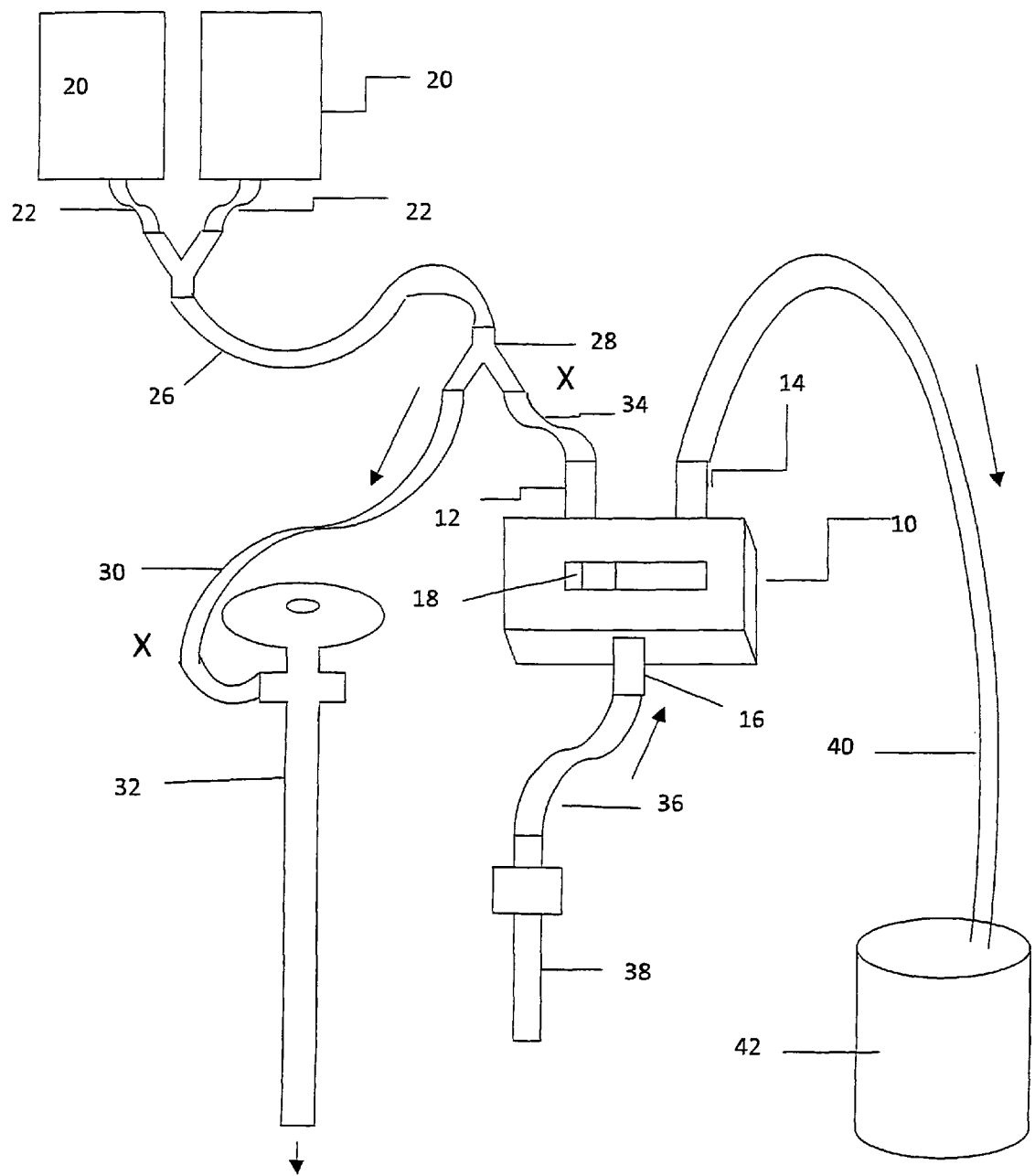
Figure 7:
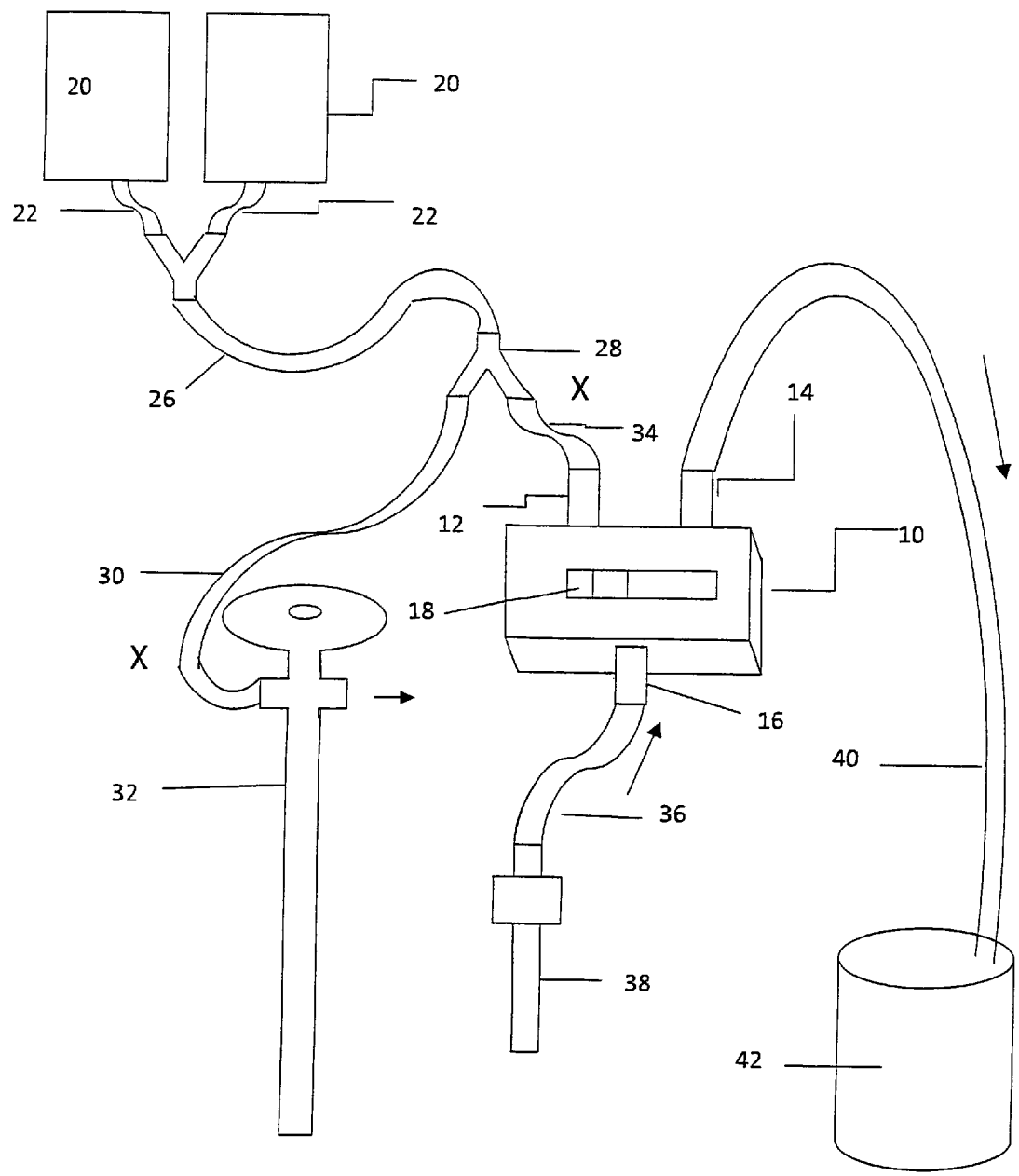
Figure 8:
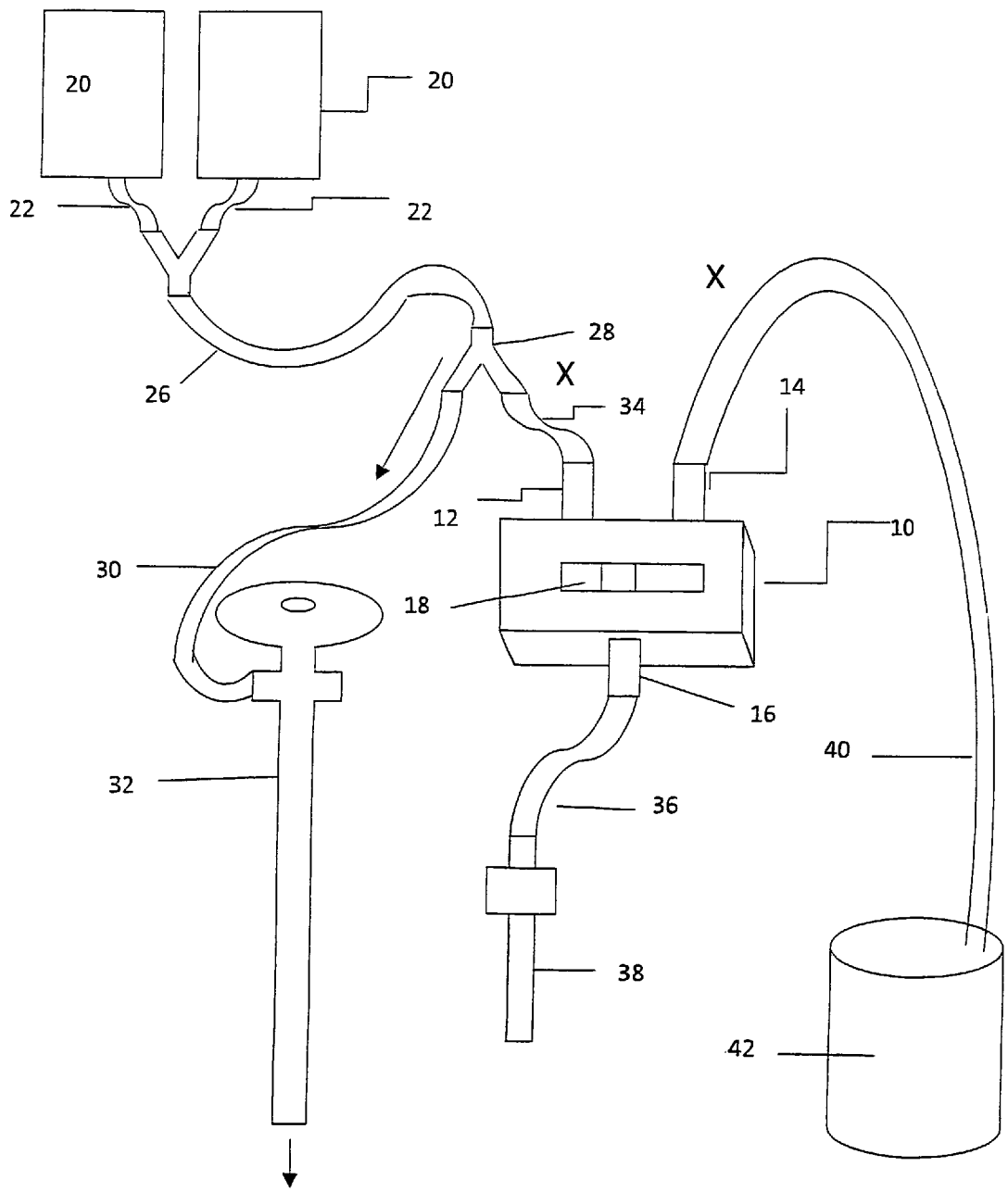

The various modes of operation of the system, including the control device 10, are seen in FIGS. 4-8. FIG. 4 shows a dual inflow operation with flow extending through ports 12 and out port 16 to the flow port cannula 38 and also having fluid flow through the arthroscope 32. The slider is moved to the right. In FIG. 5, the slide 18 is moved to the right allowing fluid flow into port 12 and out port 16 but fluid flow through the arthroscope exits out the side ports of the scope sheath. In FIG. 6 the slide 18 is moved to the left and fluid flows from the reservoir to the arthroscope 32 and drainage fluid flows up through port 16 and out port 14 to the drainage 42. In FIG. 7, the slide is moved to the left and fluid flow through the arthroscope exits the side port of the scope sheath, but fluid extends up through the flow port cannula into port 16 and out port 14, eventually to the suction drainage 42. Lastly, in FIG. 8, the slide 18 is in the middle position and fluid from the reservoir extends only through the arthroscope with no flow of fluid through the device 10.

The device allows fluid flow to be easily altered to meet the current demand, using no other driving force than gravity, although a pump could be used in conjunction with the system.

While the invention has been described with reference to a preferred embodiment, variations and modifications would be apparent to one of ordinary skill in the art. The invention encompasses such variations and modifications.

Figure 9:
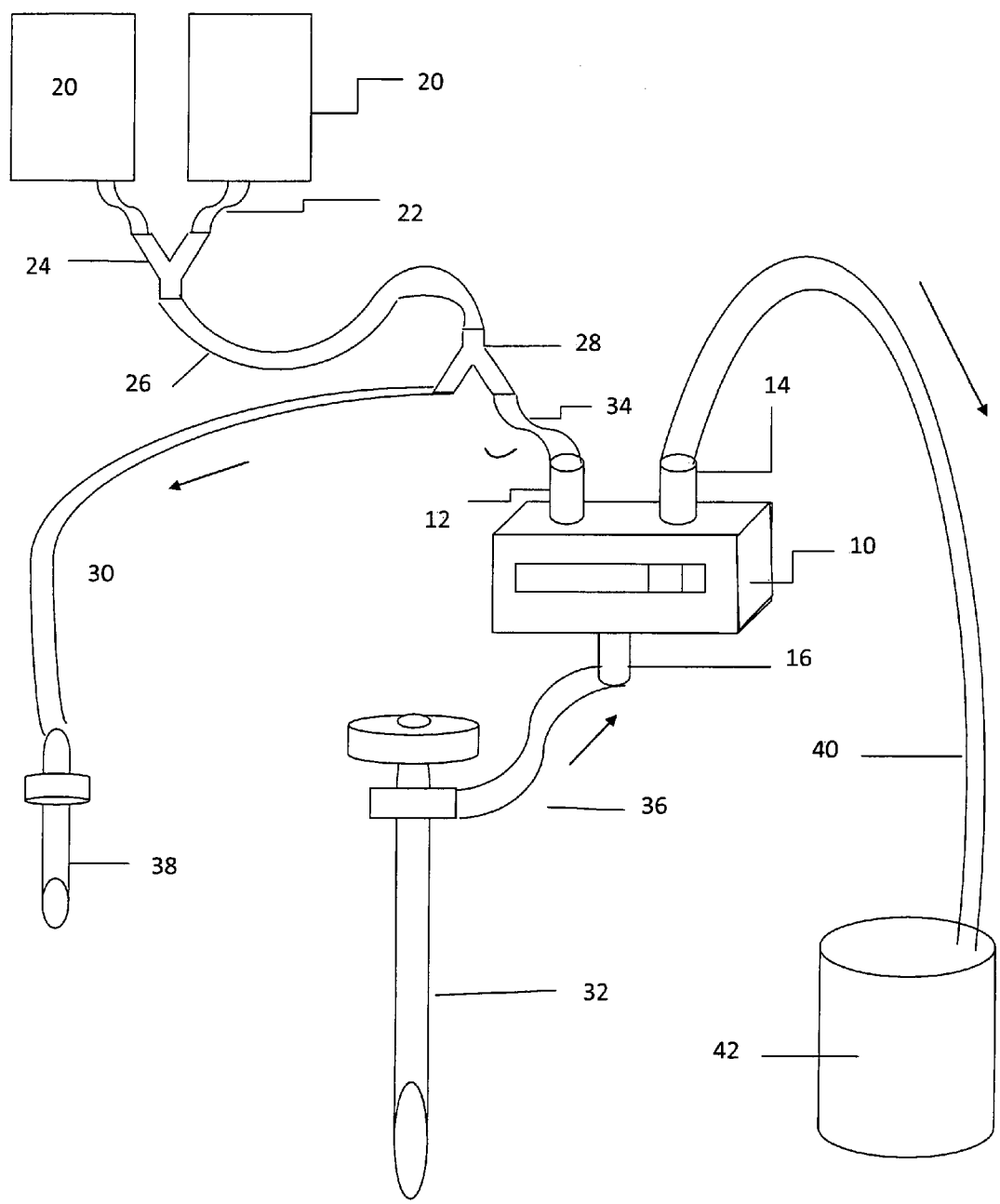
FIG. 9 is an alternate embodiment of the fluid flow control system and device.

In FIG. 9, the valve device 10 can be used in alternative configurations namely, its use or uses in multiple surgical situations or to meet the needs or preferences of a given surgeon. In this way the device could be configured with the scope 32 attached to the valve control device 10 instead of the independent cannula 38, as shown in FIG. 1.

Figure 10:
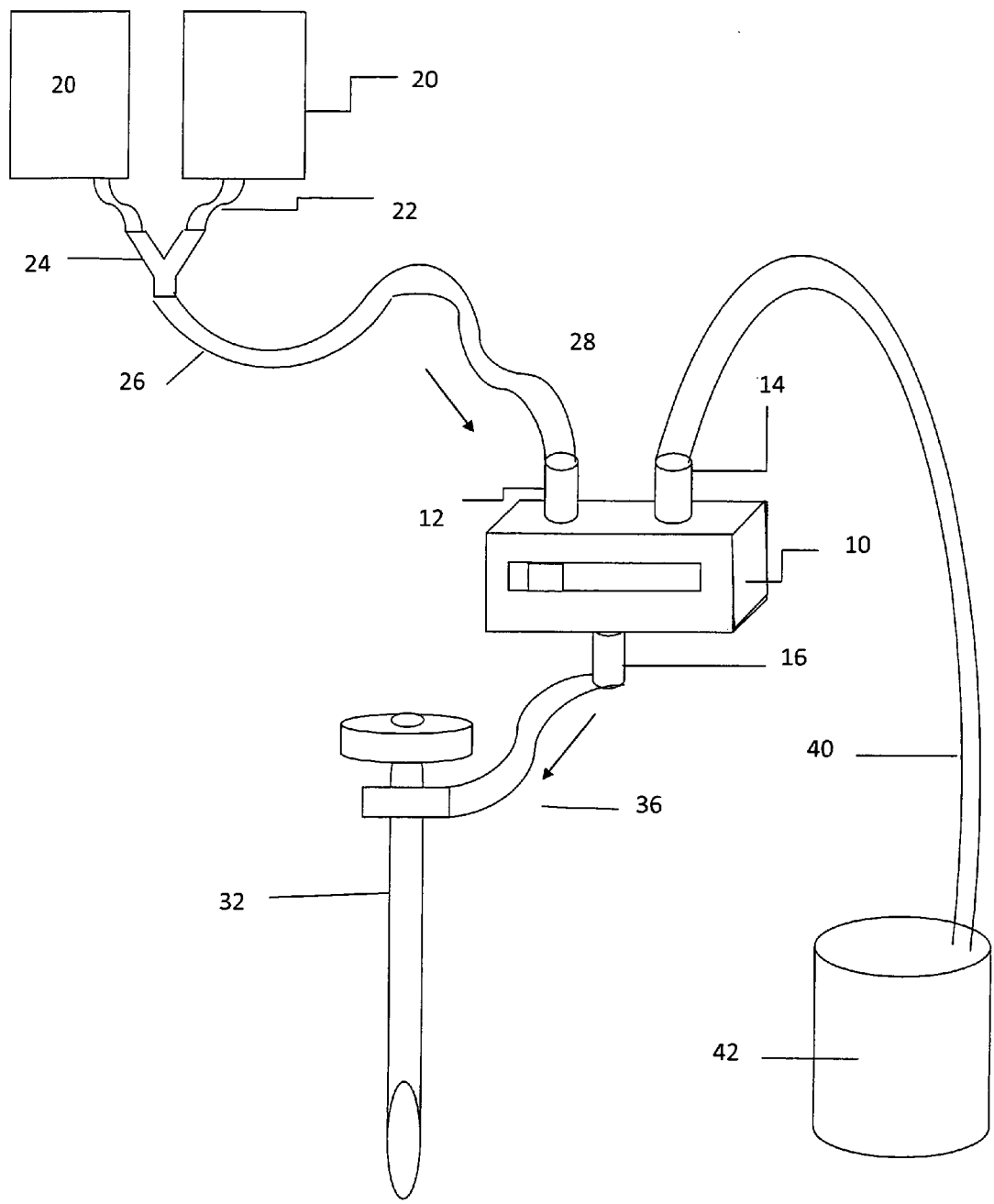
FIG. 10 is an alternate embodiment of the fluid flow control system and device.
Figure 11:
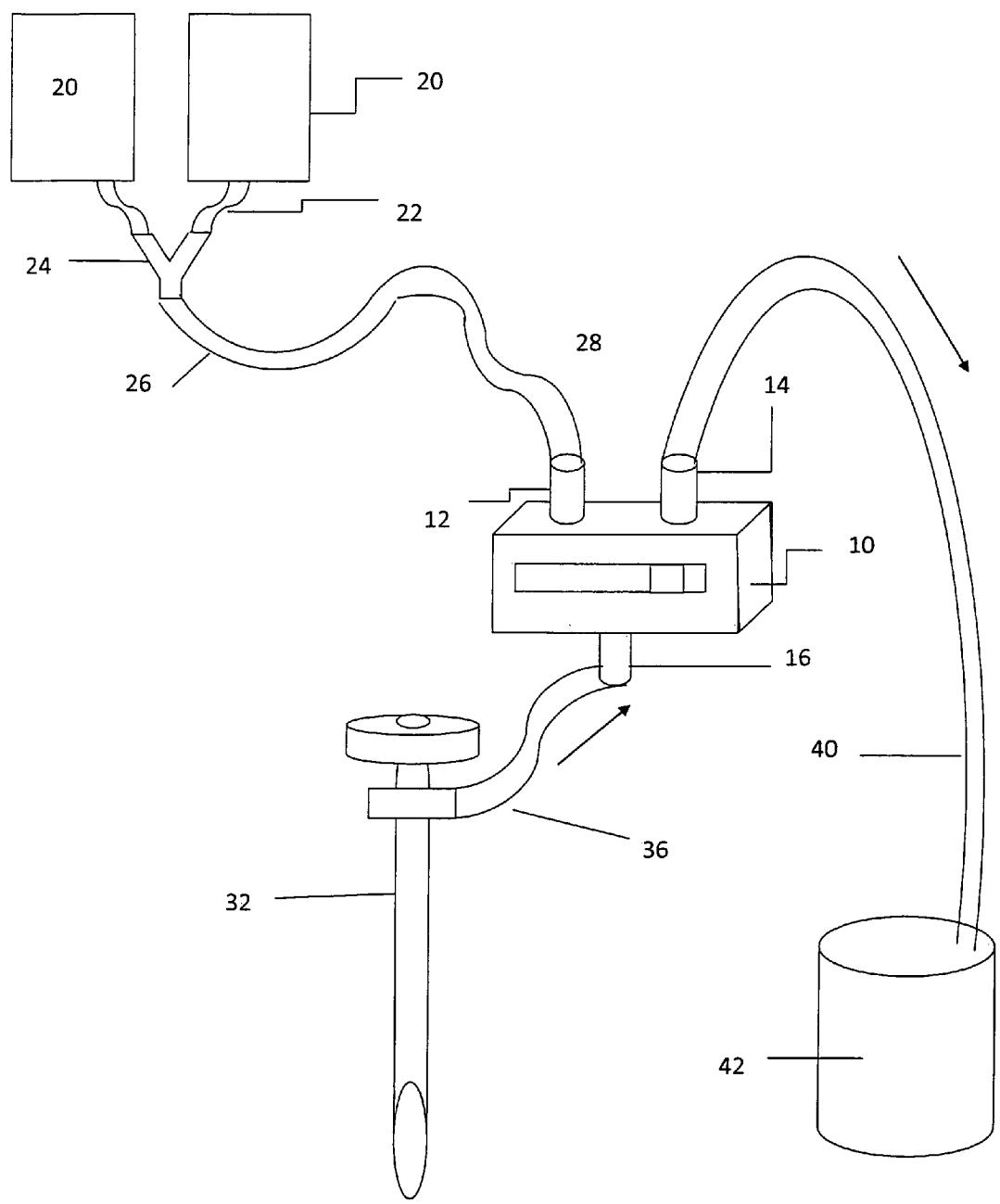
FIG. 11 is an alternate embodiment of the fluid flow control system and device.
Figure 12:
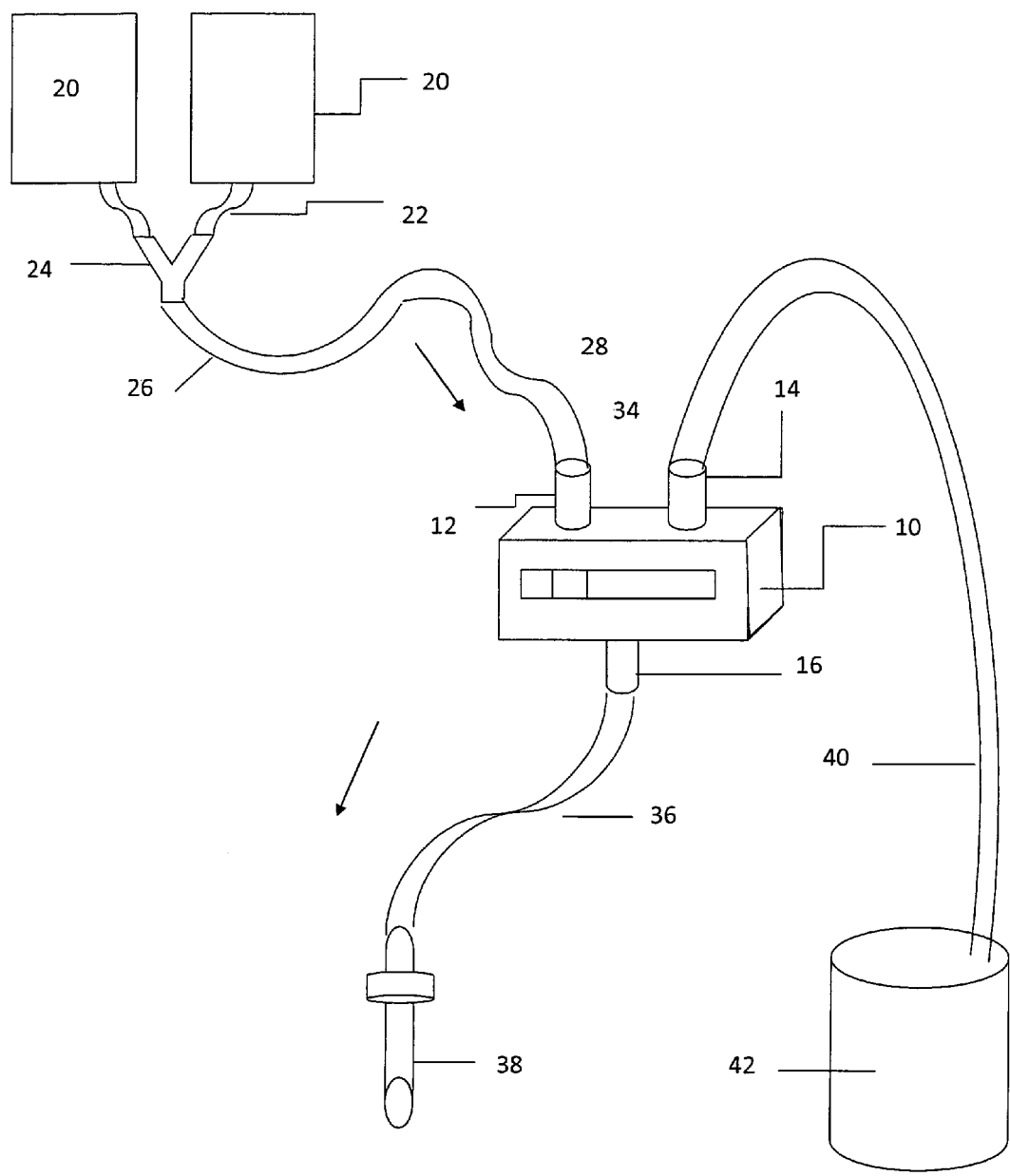
FIG. 12 is an alternate embodiment of the fluid flow control system and device.

Referring to FIGS. 10, 11 and 12, the device can be used to only control fluid into one cannula 38 or arthroscopic instrument 32. In this arrangement, the flow into and out of the scope 32 or cannula 38 in (FIG. 12), the flow rate and direction, can be controlled with one device.

Figure 13:
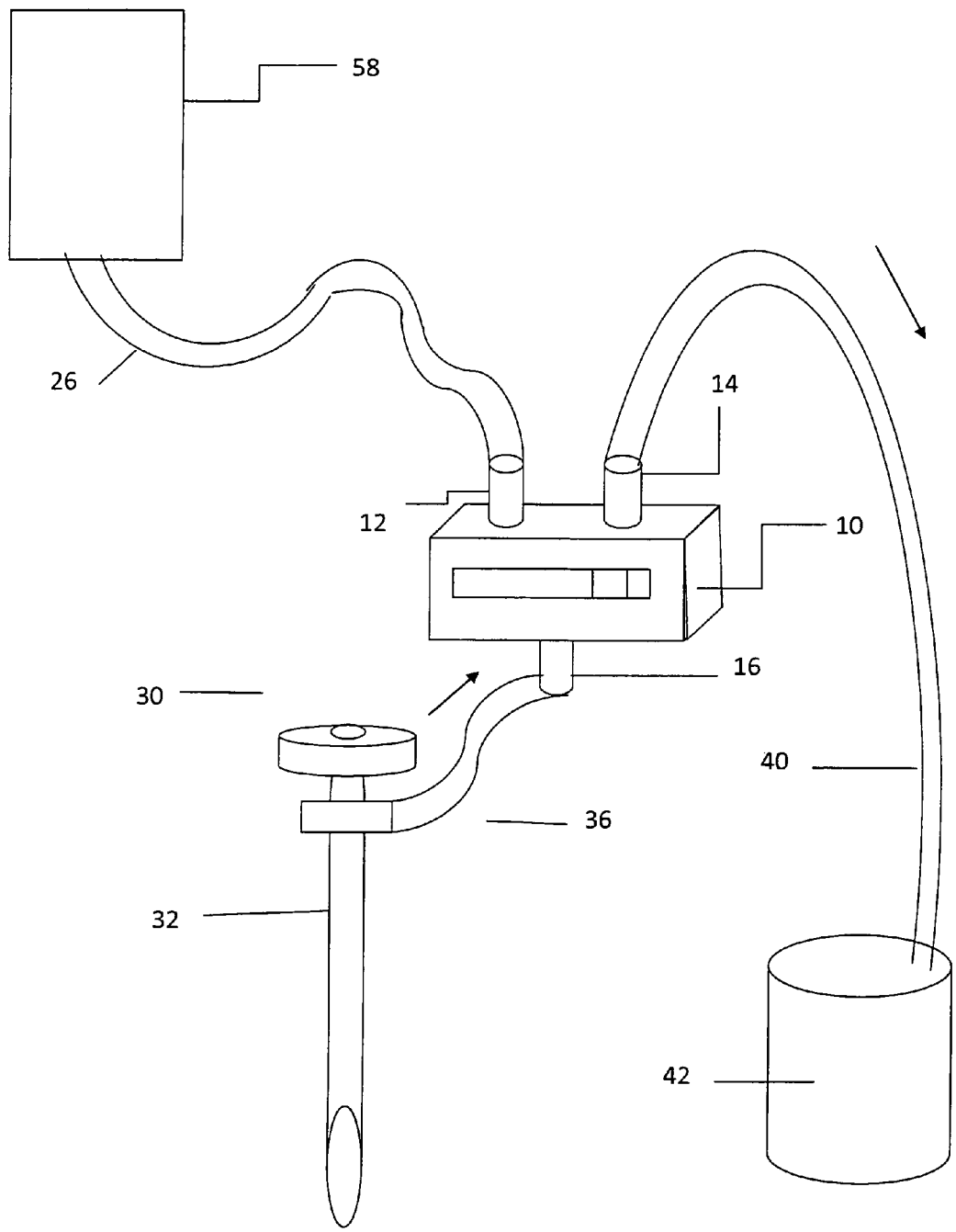
FIG. 13 is an alternate embodiment of the fluid flow control system and device.

FIG. 13 illustrates the ability to attach the fluid source 58 to one larger bag or other fluid containing device or surgeon preference. The device 10 and its configuration can be set up with one or more bags (FIG. 9) of fluid and or a single large bag for extended use.

Figure 14:
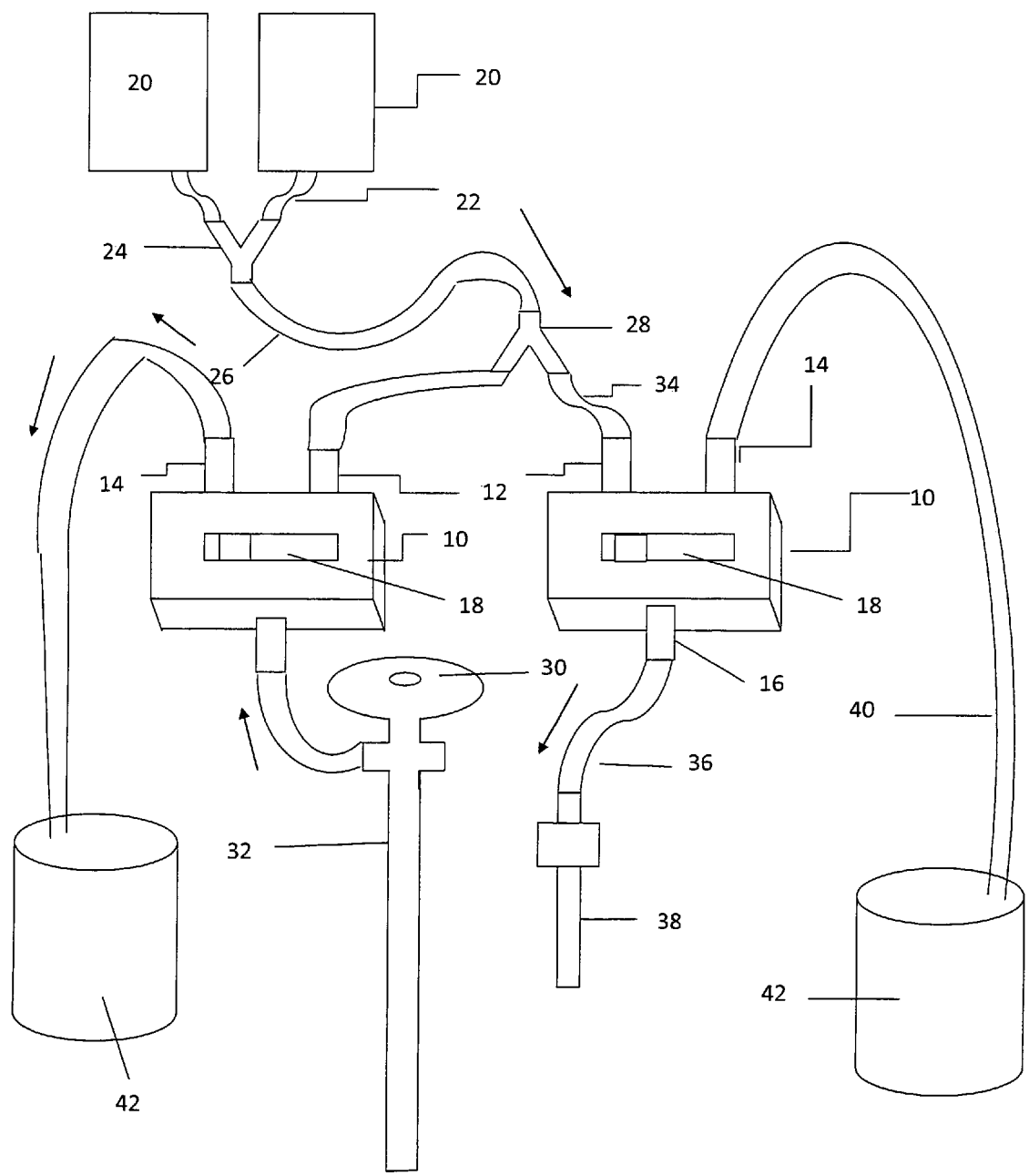
FIG. 14 is an alternate embodiment of the fluid flow control system and device.
Figure 15:
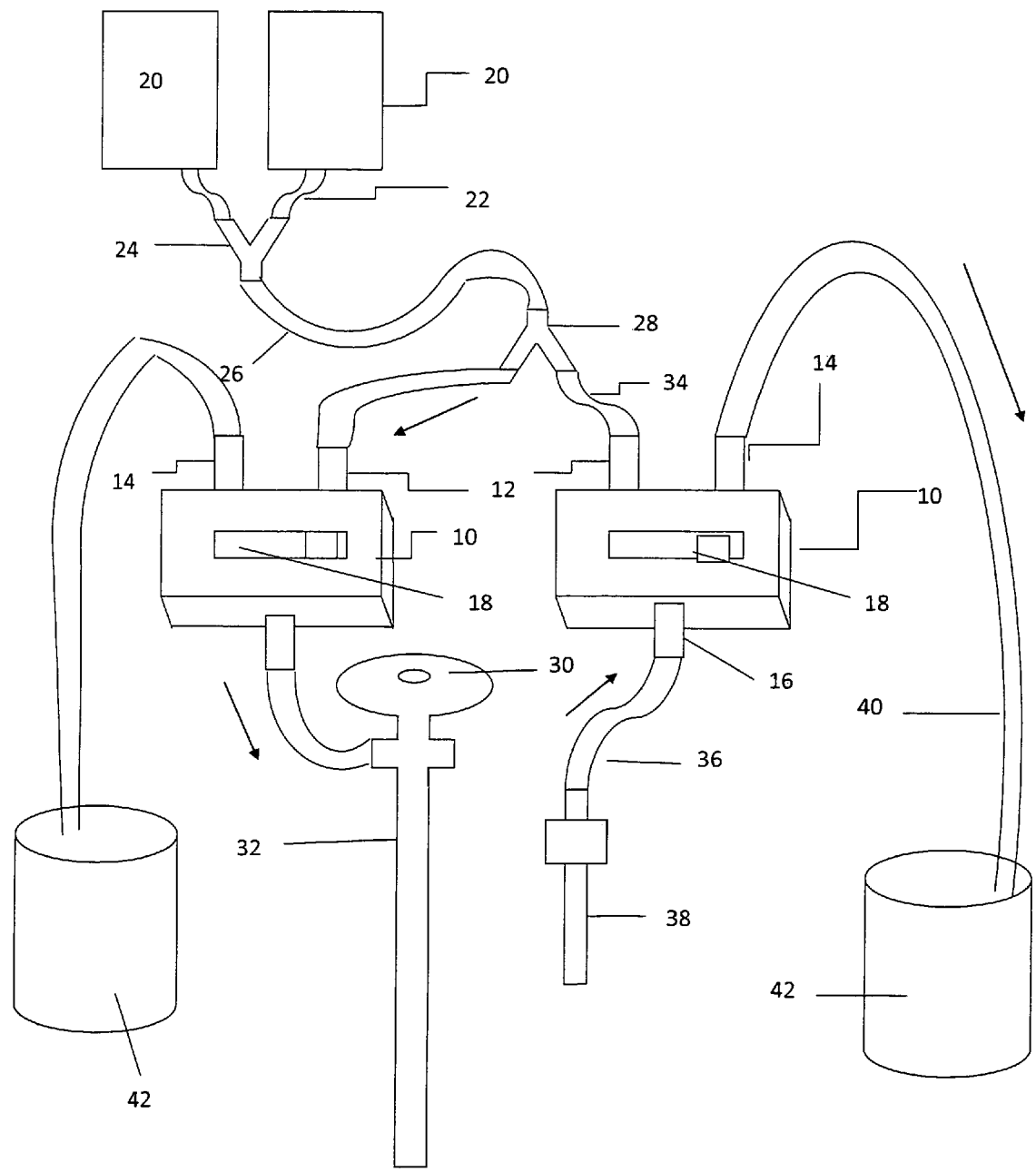
FIG. 15 is an alternate embodiment of the fluid flow control system and device.
Figure 16:
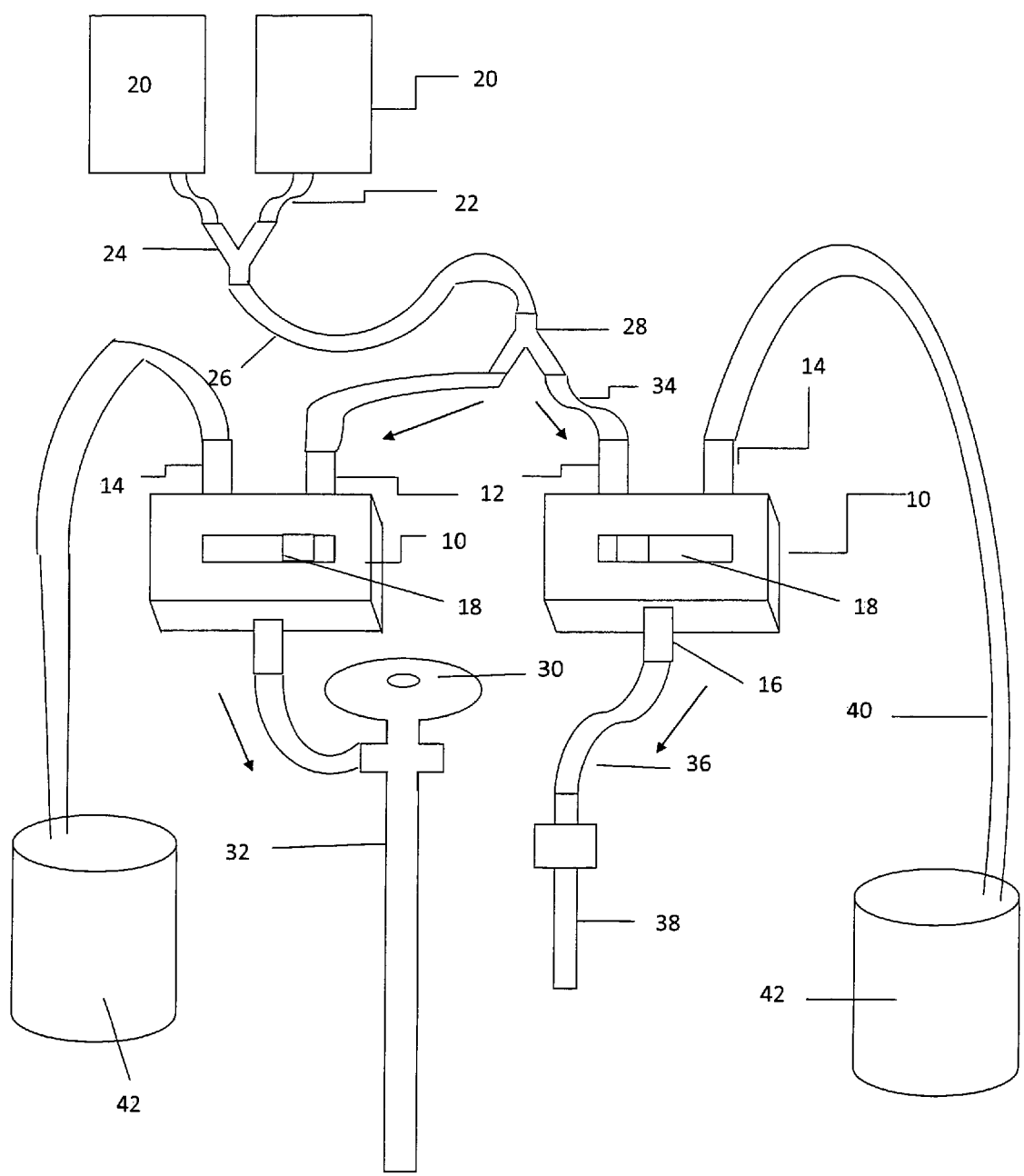
FIG. 16 is an alternate embodiment of the fluid flow control system and device.
Figure 17:
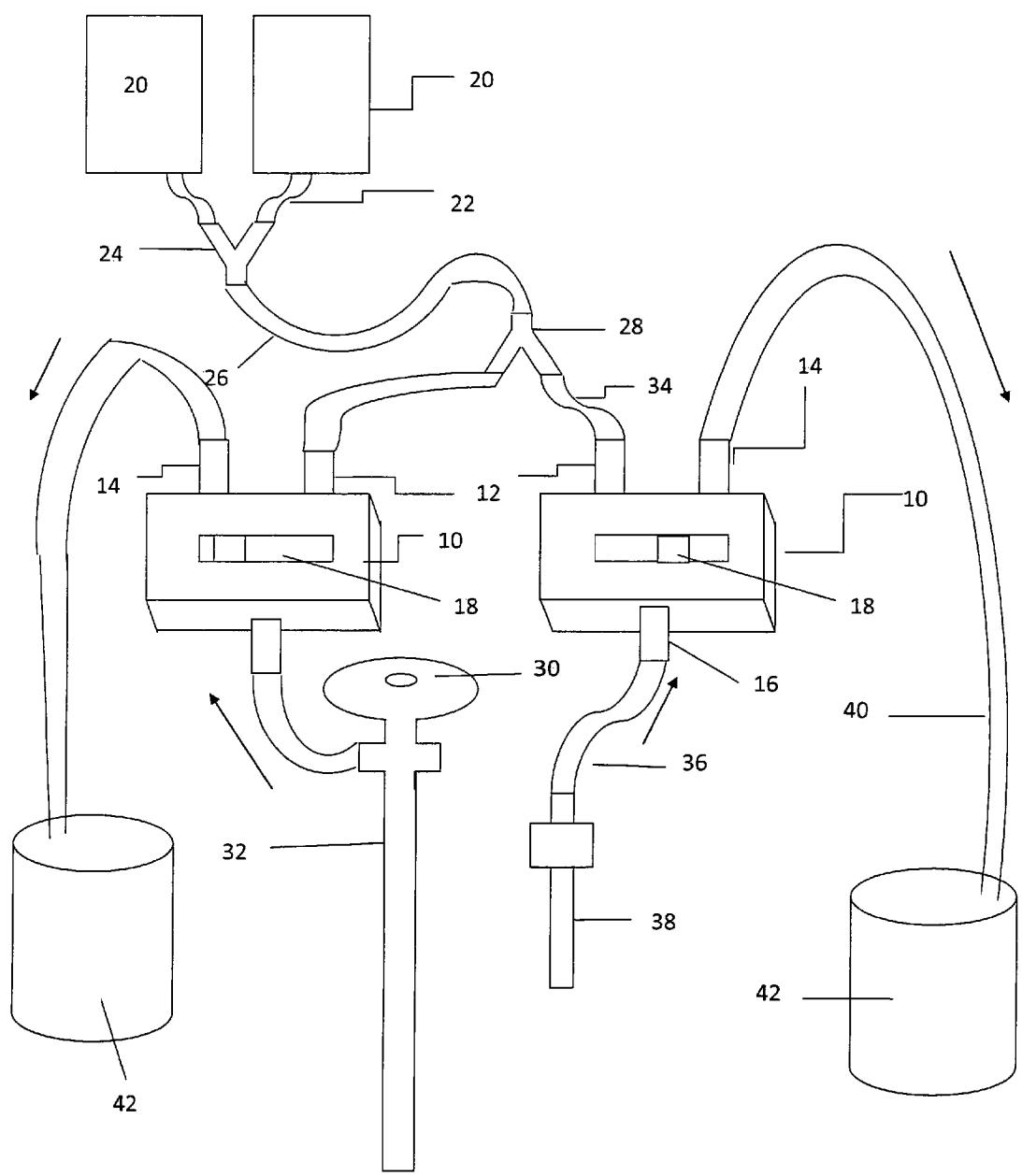
FIG. 17 is an alternate embodiment of the fluid flow control system and device.

There are also preferred configurations with more than one controller 10 (FIGS. 7, 8, 9 and 10). This allows for independent control of each port. The system can now control the rate and direction of flow into two cannulas. This allows for four different flow states along with control of fluid flow rate in each of the four flow states. They are 1—FIG. 14—Inflow to the accessory portal 38 and out the scope 32.
2—FIG. 15—Inflow to the scope 32 and out the accessory portal 38.
3—FIG. 16—Inflow into both the scope 32 and the accessory portal 38.
4—FIG. 17 Outflow into both the scope 32 and the accessory portal 38.

Figure 18:
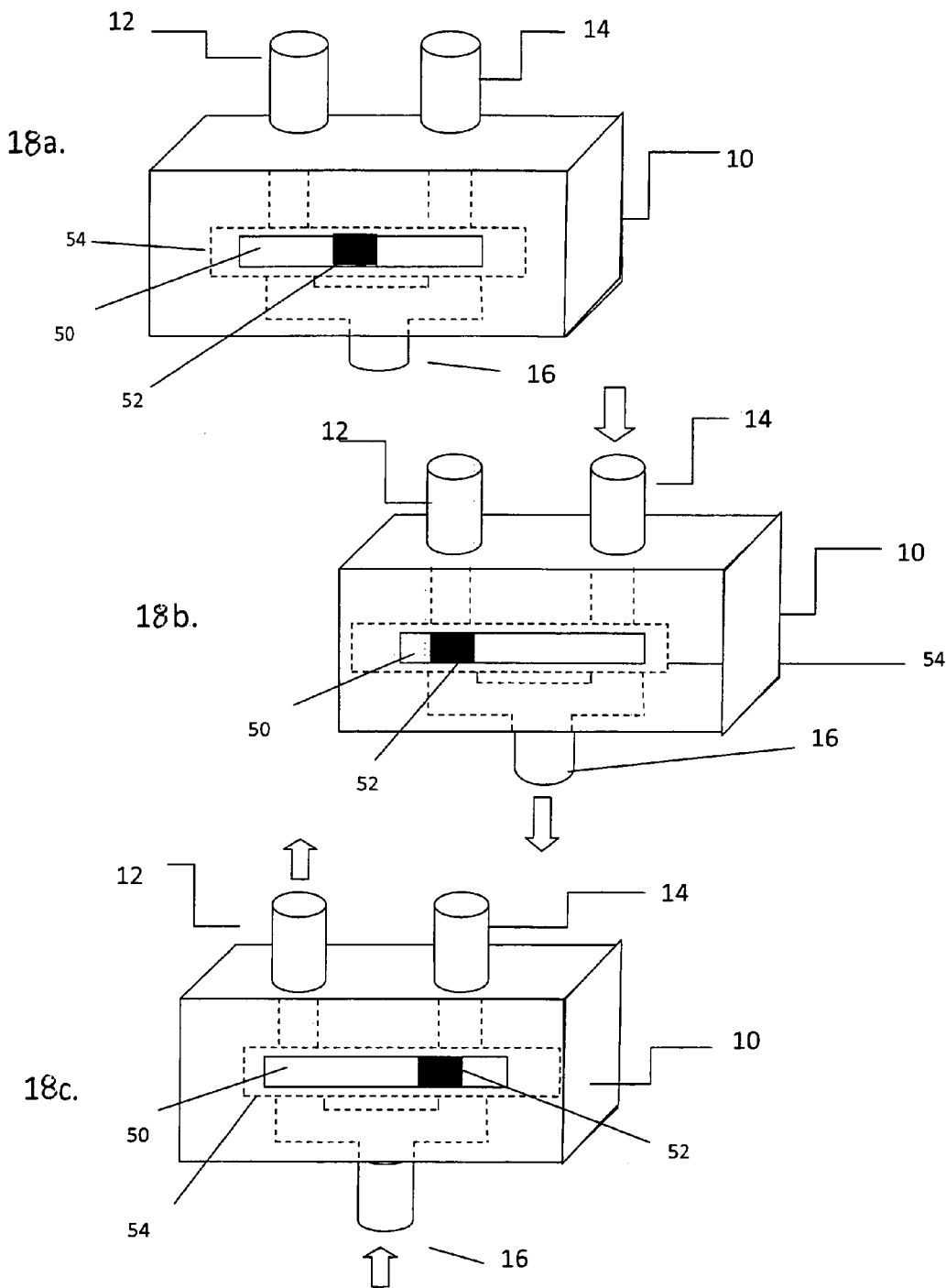
FIGS. 18*a*, 18*b*, and 18*c* show variations of the control device.
Figure 20:
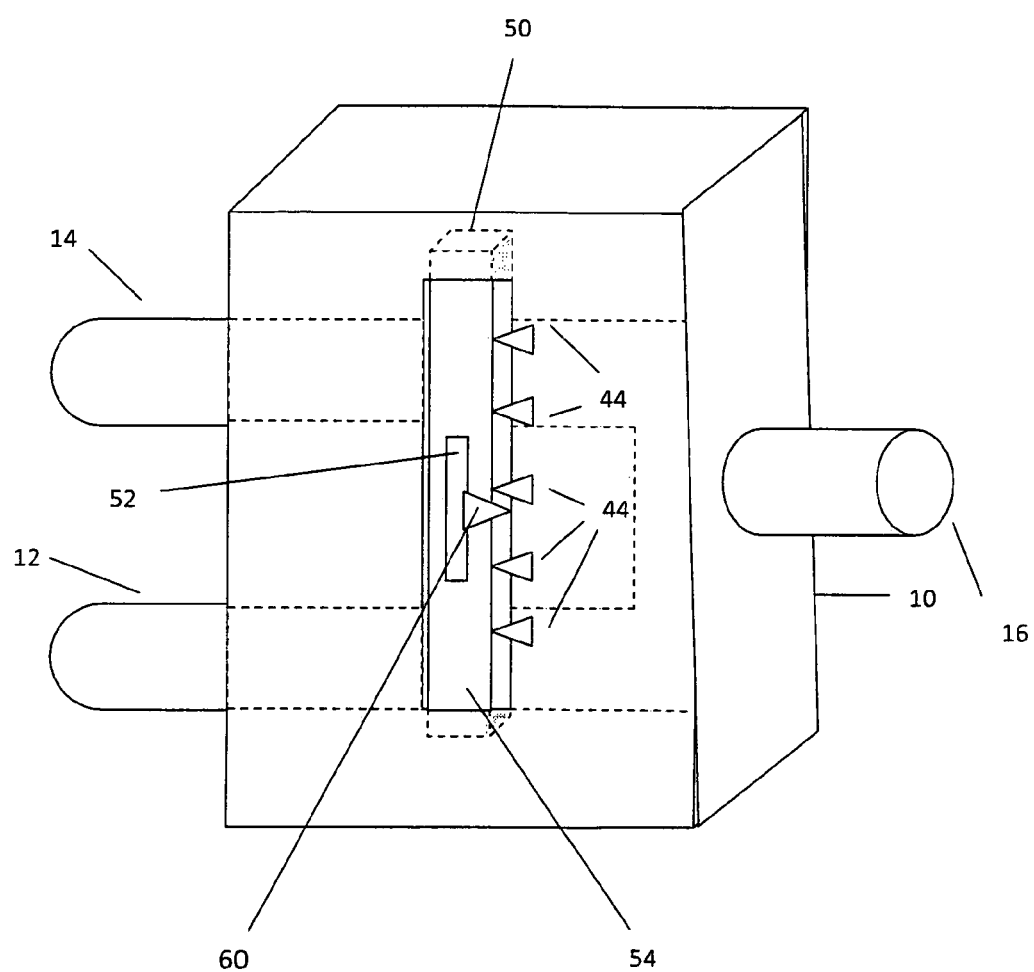
FIG. 20 shows the control device with flow markings thereon.
Figure 21A:
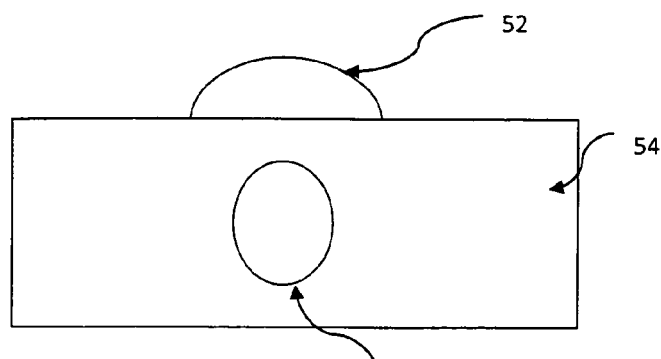
FIGS. 21*a*, 21*b*, 21*c*, and 21*d* depict variations of the slider device of the control device.
Figure 21B:
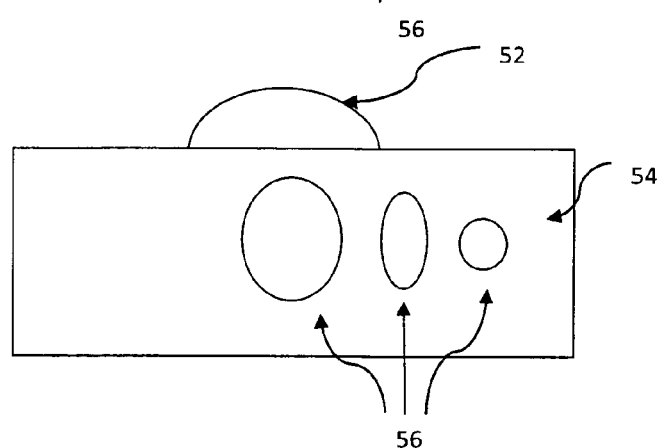
Figure 21C:
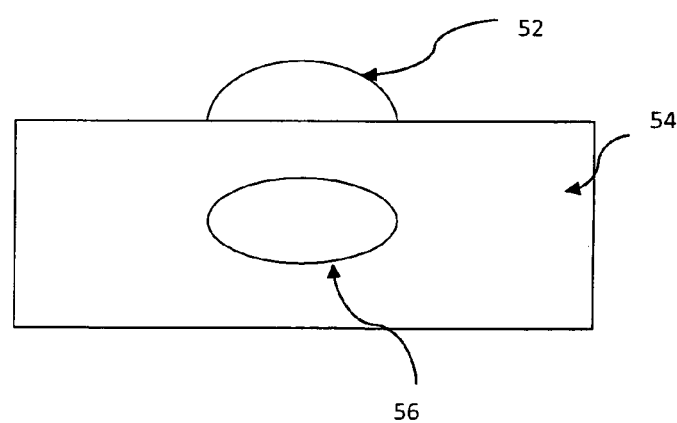
Figure 21D:
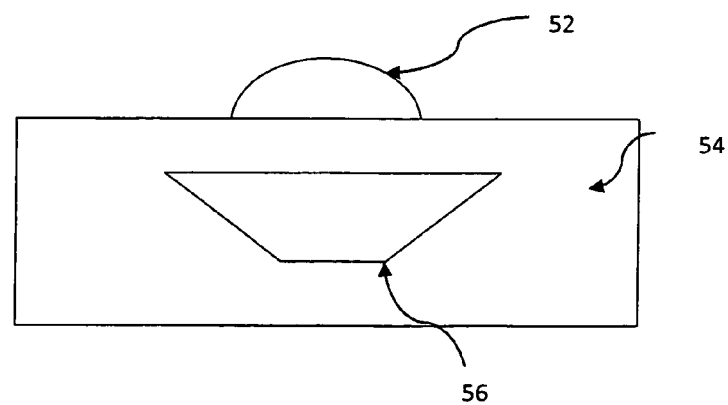

An alternative embodiment for the flow device controller 10 (FIG. 18a in the off position, 18b inflow position, and 18c out flow position) along with a new control slider (FIGS. 19a and 19b). The internal structure of the fluid controller device allows for a simpler central sliding control piece 54. As a result, this would decrease the cost of manufacture and make the device more accessible. Furthermore, the slider 54 piece has an opening with an elongated shape 56 that tapers at each end 56. This is to allow for better control of fluid rate in lower fluid flow states of operation. In FIGS. 19a and 19b The thumb control 52 has a pointer or marker on it so the control box 10 can be marked with calibration lines 44, (markings) adjoining the slider, to make the fluid control flow rates quantifiable by the user or surgeon (FIG. 20). The holes or openings in the slider device can be made of any shape, size or number (FIG. 21a-d) to best effect fluid control of any given configuration or flow rate or direction desired.

Figure 22:
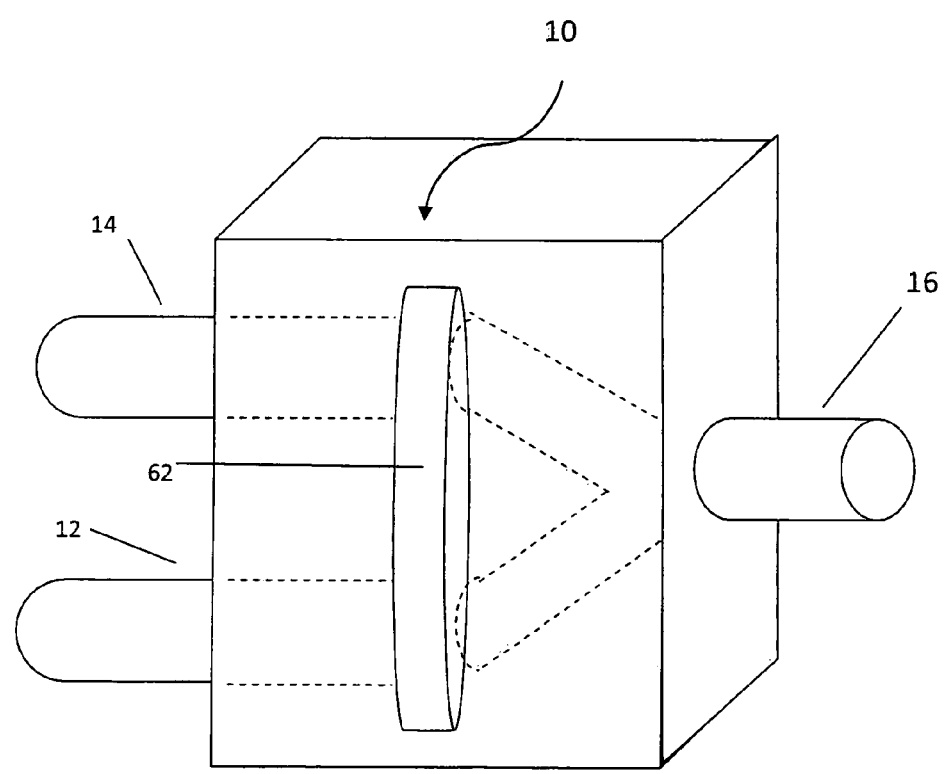
FIG. 22 displays a variation of the control device.
Figure 24A:
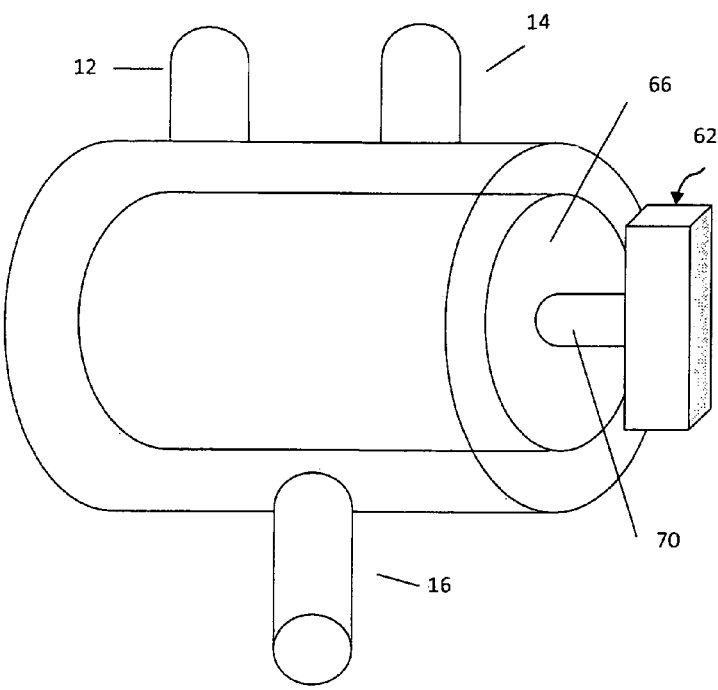
FIGS. 24*a* and 24*b* display variations of the control device.
Figure 24B:
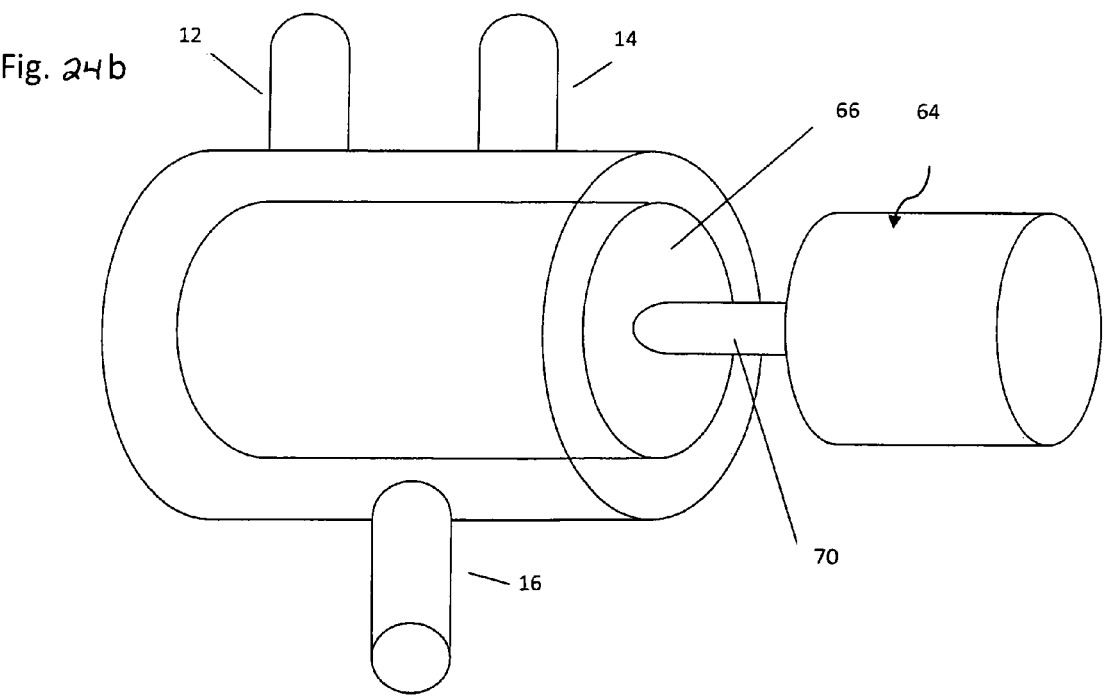

In another alternative embodiment, the control device can have various configurations. One configuration is seen in FIG. 22, which illustrates a thumb or finger wheel controller 62 instead of a thumb or figure slider device 62. This design allows for even more complexity or options on the design of the fluid control holes and modes of operation as shown in FIG. 23a-f.

Figure 25A:
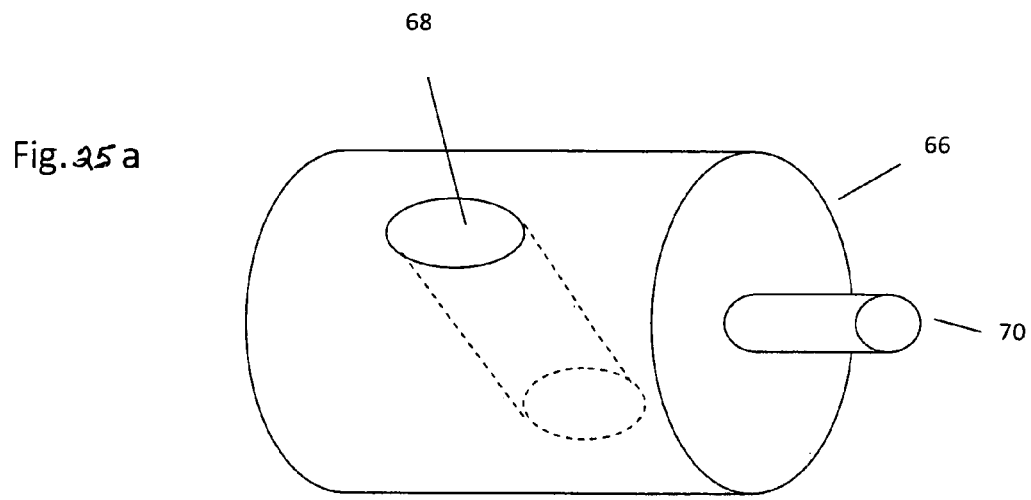
FIGS. 25*a*, 25*b*, 25*c* and 25*d* display variations of the control device.
Figure 25B:
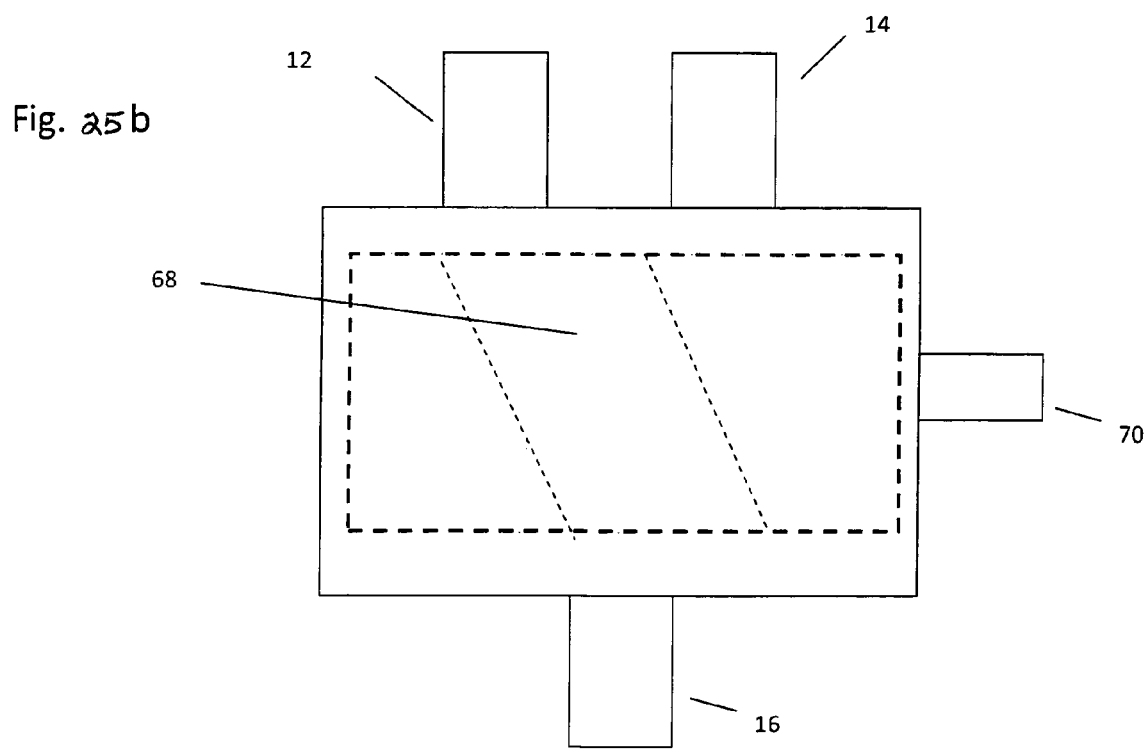
Figure 25C:
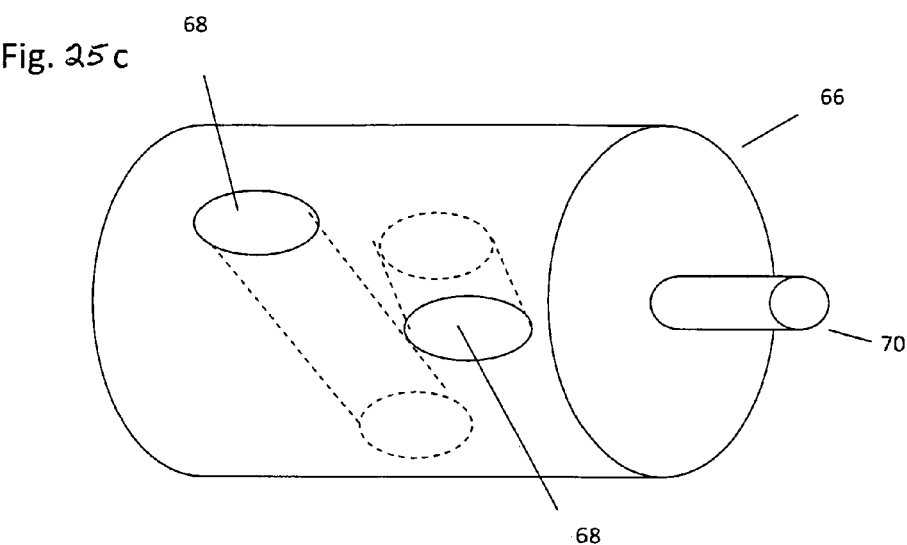
Figure 25D:
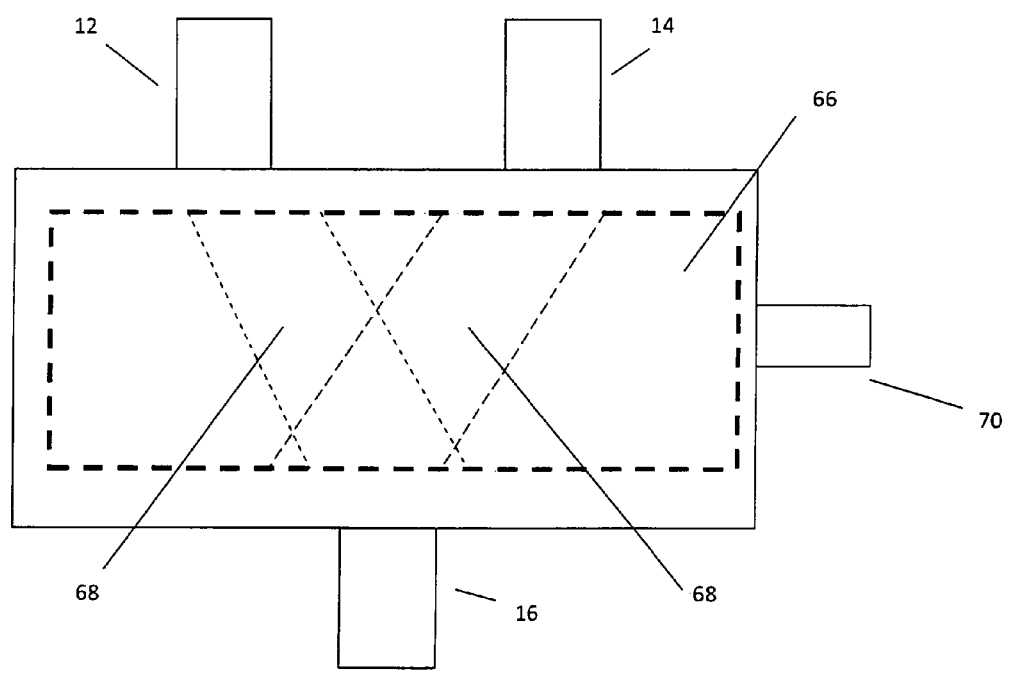

Further embodiments of the control device (FIGS. 24a, 24b, and 25a-d) are depicted that can be used with any of the prior configurations. The concept is a cylindrical controller 66 and simple rotation of a "t" handle 62 that can change direction or flow rate. In this way a simple rotation can change the direction and because a single flow control hole or opening 68 can be drilled, molded or manufactured (FIG. 25a) into the control cylinder 66 at an angle such that a 180 degree rotation of the "t" handle changes direction and rate of the fluid flow. The invention avoids the need for complex electronics, a vacuum or a pump, however this embodiment allows for a simple one way or two way variable speed servo motor 64 attached to the control shaft 70 to control the rotation and creating a new method of operation of the flow system and the possibility of truly remote control of the fluid rate and direction.

A multiple hole cylindrical controller 66 (FIGS. 18c and 18d), in this way, differing holes or openings can set up a great variety of fluid control states and settings on the device to maximize the function and the fluid control.

Various modifications or changes to the spirit of the invention are also contemplated and part of the unique fluid flow controller and method of operation.

I claim:

1. A pump and vacuum free arthroscopic fluid flow device for controlling fluid flow rate and direction into and out of a joint comprising
   at least one fluid reservoir,
   a first conduit extending from said at least one fluid reservoir, wherein the first conduit has a Y-junction, a first and second lines extending from the Y-junction, the first line leads from the Y-junction to an arthroscope,
   at least one pump and vacuum free fluid rate and flow direction controller, the fluid rate and flow direction controller having a first port, a second port and a third port, wherein the fluid rate and flow direction controller controls the flow of fluid between the second port and the first port and the fluid rate and flow direction controller controls the flow of fluid between the second port and the third port,
   the second line of the first conduit extending between the Y-junction and the first port of the fluid rate and flow direction controller,
   a second conduit extending from the second port of the fluid rate and flow direction controller, and a fluid port cannula attached to the second conduit, a third conduit connected to gravity drainage and extending from the third port of the fluid rate and flow directional controller, the at least one fluid rate and flow direction controller is a valve including a slider device movable between a first position, a second position and a third position to enable various flow rates to be achieved, wherein a first mode of operation is provided when the slider is placed in the first position allowing fluid flow between the first conduit and the second conduit and preventing fluid flow from the second conduit to the third conduit, a second mode of operation is provided when the slider is placed in the second position allowing a desired amount of fluid flow from the second conduit to the third conduit and preventing a desired amount of fluid flow from the first conduit to the second conduit, and a third mode is provided when the slider is placed in the third position preventing all fluid flow through the at least one fluid rate and flow direction controller.

2. The fluid device of claim 1, wherein the at least one fluid rate and flow direction controller has tapered cones connecting elements to facilitate the attachment of various flow tube diameters.

3. The fluid device of claim 1, wherein the slider device of the at least one fluid rate and flow direction controller comprises at least one opening for enabling a flow of fluids.

4. The fluid device of claim 1, wherein the slider device of the at least one fluid rate and flow direction controller has one elongated shaped opening with tapered ends approximately in the shape of a hexagon.

5. The fluid device of claim 4, wherein the one opening of the slider device of the at least one fluid rate and flow direction has a width of 1 cm and a height of 6 mm.

6. The fluid device of claim 1, wherein the at least one fluid rate and flow direction controller further comprises markings adjoining the slider element to enable a user to select various flow and direction rates.

7. The fluid device of claim 1, wherein the slider device of the at least one fluid rate and flow direction controller is in the shape of a cylinder with at least one opening.

8. A method of controlling the fluid flow rate into and out of a joint during an arthroscopic procedure comprising the steps of adjusting the fluid flow rate into and out of the joint using the device as claimed in claim 1, without a pump, vacuum, electronic fluid controller or feedback loop device.

9. The method of claim 8, wherein outgoing fluid flowing into the drainage line is caused by gravity or a positive pressure environment in the joint.

10. The method of claim 8, wherein the at least one fluid rate and flow direction controlling slider device is placed in various positions between the first position and the third position allowing partial flow in either direction through the at least one fluid rate and flow direction controller.

* * * * *